United States Patent [19]

Shepherd

[11] 4,333,940

[45] Jun. 8, 1982

[54] RING-FLUORINATED 4-(MONOSUBSTITUTED-AMINO) PHENYL COMPOUNDS IN INHIBITING ATHEROSCLEROTIC LESION DEVELOPMENT

[75] Inventor: Robert G. Shepherd, South Nyack, N.Y.

[73] Assignee: American Cyanamid Company, Stamford, Conn.

[21] Appl. No.: 176,958

[22] Filed: Aug. 11, 1980

Related U.S. Application Data

[62] Division of Ser. No. 874,433, Feb. 2, 1978, Pat. No. 4,243,609.

[51] Int. Cl.³ .................... A01N 41/02; A01N 43/42; A61K 31/44; A61K 31/255
[52] U.S. Cl. .................................. 424/263; 424/270; 424/283; 424/303; 424/307; 424/317; 424/320
[58] Field of Search ............... 424/263, 270, 283, 303, 424/307, 317, 321

[56] References Cited

U.S. PATENT DOCUMENTS

| | | | |
|---|---|---|---|
| 3,245,913 | 4/1966 | Matzner | 564/87 X |
| 3,340,297 | 9/1967 | Seefelder | 564/87 X |
| 3,787,478 | 1/1974 | Dolejs et al. | 564/87 X |
| 3,868,416 | 2/1975 | Albright | 564/87 |
| 4,036,977 | 7/1977 | Lednicer | 424/274 |
| 4,133,890 | 1/1979 | Wagner et al. | 424/282 |
| 4,143,151 | 3/1979 | Wagner et al. | 424/275 |

*Primary Examiner*—Floyd D. Higel
*Attorney, Agent, or Firm*—Robert P. Raymond

[57] ABSTRACT

The present invention relates to the use of certain ring-fluorinated 4-(monosubstituted-amino) phenyl compounds as hypolipidemic and antiatherosclerotic agents together with their pharmacologically acceptable acid-addition and cationic salts.

12 Claims, No Drawings

RING-FLUORINATED 4-(MONOSUBSTITUTED-AMINO) PHENYL COMPOUNDS IN INHIBITING ATHEROSCLEROTIC LESION DEVELOPMENT

This is a division of application Ser. No. 874,433, filed Feb. 2, 1978, now U.S. Pat. No. 4,243,609.

BRIEF SUMMARY OF THE INVENTION

This invention relates to new organic compounds and, more particularly, is concerned with ring-fluorinated 4-(monosubstituted-amino)substituted phenyl compounds which may be represented by the following structural formula

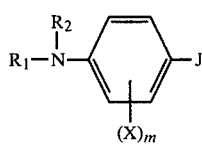

wherein $R_1$ is a saturated or unsaturated hydrocarbon radical of 7-19 carbon atoms which may be branched or unbranched and which may contain one or more radicals selected from the group consisting of saturated or unsaturated cycloalkyl, substituted or unsubstituted aryl and substituted or unsubstituted heteroaryl; $R_2$ is selected from the group consisting of hydrogen or a group convertible in vivo thereinto such as methyl, carboxymethyl, acetyl, succinyl, 1-(sodiumsulfo)loweralkyl, 1-(sodiumsulfo)polyhydroxyalkyl, and 3-aryl-1,3-bis-(sodiumsulfo)alkyl; X is selected from the group consisting of loweralkyl, loweralkoxy, hydroxy, nitro, acyloxy and halo; and m is an integer from 1 to 4, inclusive; and (a) J is

Z is selected from the group consisting of hydrogen, loweralkyl, hydroxy, loweralkoxy, loweralkoxyalkoxy, di-loweralkylaminoalkoxy, (mono- or polyhydroxy)-loweralkoxy, allyloxy, 2,3-epoxypropoxy, substituted or unsubstituted benzyloxy, substituted or unsubstituted phenoxy and 3-pyridyloxy, pyridylmethoxy, (mono- or polycarboxy)loweralkoxy, (mono- or polycarboxy)hydroxyloweralkoxy, tetrahydropyranyloxy, (mono- or polyhydroxy)alkylamino, allylamino, propargylamino, 2-sulfoethylamino, (mono- or polycarboxy)loweralkylamino, (mono- or polycarboalkoxy)loweralkylamino, loweralkanoylamino, (substituted or unsubstituted-)aroylamino, loweralkanesulfonylamino, (substituted or unsubstituted)arenesulfonylamino, loweralkanoylhydrazino, hydroxylamino, polymethyleneimino, 4-carboethoxy- or 4-carboxythiazolidino, lower alkyl bearing one or more carboxy, carboalkoxy, carbamoyl, acyl, sulfinyl, or sulfonyl groups, or (d) J is carboxy loweralkyl, carboxyloweralkenyl, carboxyloweralkynyl, carboalkoxyloweralkyl, carboalkoxyloweralkenyl, carboalkoxyloweralkynyl; and the pharmaceutically acceptable non-toxic acid-addition and cationic salts thereof. Lower whenever applied to alkyl, alkoxy, alkenyl or alkynyl refers to a chain of 1-4 carbon atoms which may be branched or unbranched.

Included within the scope of this invention are ring-fluorinated 4-(disubstituted amino)phenyl compounds wherein the substituent $R_2$ can be converted in vivo to hydrogen. Included among such substituents are, for example, methyl, carboxymethyl, acetyl, succinyl, 1-(sodium sulfo)lower alkyl, 1-(sodiumsulfo)polyhydroxy alkyl, and 1,3-bis(sodium sulfo)aralkyl.

Suitable groups contemplated by the present invention for the substituent $R_1$ are saturated or mono- or poly-olifinic or acetylenic such as n-undecyl; n-tetradecyl; n-hexadecyl; n-octadecyl; 1-methylundecyl; 1-methylpentadecyl; 1-methylhexadecyl; 1-ethyltetradecyl; 2-methylundecyl; 2-methylpentadecyl; 6-methylhexadecyl; 14-methylpendacyl; 15-methylhexadecyl; 3,7,11-trimethyldodecyl; 3,7,11,15-tetramethylhexadecyl; 1-methyl-1-ethyl-tetradecyl; 1,1-dimethylundecyl; 1,1-dimethyltetradecyl; 13,13-di-methyltetradecyl; 15,15-dimethylhexadecyl; 10-undecenyl; 3,7-dimethyl-6-octenyl; 2,6,10-trimethyl-11-dodecenyl; 1-methyl-6-heptenyl; 1,1-diisopropyl-2-propenyl; 1,3-dimethyl-1-ethyl-2-pentenyl; 4,14-pentadecadienyl; 3,7,11-trimethyl-2,6,10-dodecatrienyl; 11-hexadecynyl; 6-methyl-6-hepten-2-ynyl; 1-isopropyl-1-methyl-2-heptynyl; 3-(1,3-dimethylcyclohexyl0-2-propyl; 13-cyclo-pentyltridecyl; 11-cyclohexylundecyl; cyclotetradecyl; 4-(1-cyclohexenyl)butyl; 4-cyclohexyl-2-butenyl; 11-phenylundecyl; 4-chlorobenzyl; 3-(4-fluorophenyl)propyl; 6-(4-methoxyphenyl)hexyl; 4-(decyloxy)benzyl; 4-methylbenzyl; 3-(3-trifluoromethylphenyl)propyl; 3-fluoro-4-methylbenzyl; 3-(4-chloro-2-methoxyphenyl)propyl;- cinnamyl; 4-(2-thienyl)butyl; 6-(2-furyl)hexyl; 3-(5-methyl-2-furyl)propyl; 3-(2,4-dichlorophenyl)propyl; 3-(4-benzyloxyphenyl)propyl; 2-(1-naphthyl)ethyl and the like.

Various mono- and poly-substituted 4-(monosubstituted amino)phenyl compounds are contemplated by the present invention. These include phenyl compounds in which the group $(X)_m$ represents 2methyl; 3-methyl; 3,5-dimethyl; 2-chloro; 3-chloro; 3,5-dichloro; 3,5-dibromo; 3,5-diiodo; 2-hydroxy; 3-hydroxy; 2-acetoxy; 2-methoxy; 3,5-dimethoxy; 3-bromo; 3-nitro, 2-fluoro; 3-fluoro; 2,5-difluoro; 2,6-difluoro; 3,5-difluoro; 2,3,5-trifluoro; 2,3,6-trifluoro; or 2,3,5,6-tetrafluoro and the like.

Suitable esters contemplated by the present invention are those in which the group Z is methoxy; isopropoxy; 2-ethoxyethoxy; 2-dimethylaminoethoxy; 1-methyl-4-piperidyloxy; 4-pyridylmethoxy; 2,3-dihydroxypropoxy; 2-hydroxypropoxy; 3-hydroxypropoxy; 4-chlorobenzyloxy; 3-methylbenzyloxy; 4-sulfophenoxy; 4-fluorophenoxy; 2,6-dichlorophenoxy; 3-carboxyphenoxy; 2,6-dimethyl-3-pyridyloxy; 6-methoxy-3-pyridyloxy; 2-hydroxy-3-pyridyloxy; 5-carboxy-3-pyridyloxy; 4-cyano-3-pyridyloxy; carboxymethoxy; 1-methoxycarbonylpropoxy; 2-methoxycarbonyl-2-propyl and the like.

Suitable amides contemplated are those in which the group Z is 2,3-dihydroxypropylamino; carboxymethylamino, acetylamino, benzoylamino, 4-chlorobenzoylamino; methanesulfonylamino; phenylsulfonylamino, 1-piperidyl, and the like.

Suitable keto-acids and keto-esters contemplated by the present invention are those in which the radical Z is selected from the group consisting of carboxymethyl; carboxyethyl; 2-carboethoxy-2-propyl; dicarboethoxymethyl; carboethoxyvinyl and the like. Suitable alkanoic, alkenoic and alkynoic acids and esters are those in which the radical J is selected from the group consisting of 4-carboxybutyl; 2-carboethoxyethyl; 2-carboxyvinyl, 2-carboethoxyethynyl, and the like.

The invention also pertains to novel compositions of matter useful as antiatherosclerotic agents and to methods of ameliorating atherosclerosis by counteracting hyperlipemia and arterial plaque formation in mammals therewith; the active ingredients of said compositions of matter being the novel ring fluorinated 4-(monosubstituted-amino)phenyl compounds of the present invention. These compounds may be utilized either as the free bases or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gorden and Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson and Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine, and nicotinic acid [Levy and Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis. Related compounds are the subject of our copending U.S. Patent Applications Ser. Nos. 26,901; 26,902; 26,904, 26,905; 26,898 and 25,650 as well as U.S. Pat. No. 3,868,416 issued Feb. 25, 1975.

DETAILED DESCRIPTION OF THE INVENTION

The compounds of this invention are new and novel ring-fluorinated 4-(monosubstituted-amino)phenyl compounds and have useful biological and pharmacological properties. No hypolipidemic activity has been reported in the literature for these compounds and they are different in structure from other hypolipidemic agents. The compounds of this invention lower serum-lipid concentrations and also minimize atheroma formation in the aorta. These compounds provide the oral administration required of hypolipidemic agents, which patients usually take for many years. The novel compounds of this invention are adequately and reliably absorbed from the gastrointestinal tract with little, if any gastrointestinal irritation.

We have now found that certain members of this class of compound can safely and effectively lower both serum sterols and triglycerides in warm-blooded animals. Such actions on serum lipid components are considered to be very useful in the treatment of atherosclerosis, especially in contrast to available drugs whose action is much more limited. For some time it has been considered desirable to lower serum-lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The ring fluorinated 4-(monosubstituted-amino)phenyl compounds of the present invention are, in general, white crystalline solids having characteristic melting points and absorption spectra. They are soluble in organic solvents such as lower alkanols, chloroform, toluene, dimethylformamide, and the like but are generally not very soluble in water.

The novel compounds of the present invention which are organic bases may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like.

The novel compounds of the present invention in their acidic forms or those which contain acidic substituents are converted to their organic or inorganic cationic salts for therapeutic use. The sodium or potassium salts which are formed in solution in the course of hydrolysis of their esters can be isolated as the solid alkali metal salts by cooling. Where it is desirable to purify a compound in the form of the acid, the salt is conveniently formed by treating its solution with exactly one equivalent of base and evaporation or lyophilization. Alkaline earth salts are prepared similarly, often using their acetate salts as a conveniently soluble form. Organic base salts such as those of N-methylglucamine are prepared by dissolving equimolar amounts of the acid and the base in hot ethanol or aqueous alcohols and cooling to crystallization.

(Mono- or poly-fluoro)-4-aminophenyl compounds required as intermediates for the preparation of the novel (mono- or poly-fluoro)-4-(monosubstituted amino)phenyl compounds of the present invention are obtained by a variety of methods. The 4-amino-(mono- or poly-fluoro)benzoic acids are obtained by oxidation of the corresponding N-protected toluenes, for example 4-acetamido-2-fluorotoluene, with potassium permanganate. The 4-amino-(mono- or poly-fluoro)benzoate esters are obtained by reactions of ammonia or sodium amide with a 4-halo-benzoate ester. For example, the reaction of sodium amide with ethyl 2,3,4,5,6-pentafluoro benzoate yields ethyl 4-amino-2,3,5,6-tetrafluorobenzoate.

The [4-amino(mono- or poly-fluoro)phenyl]alkanoic acids and esters required as intermediates are prepared by a sequence of reactions involving nitration of a suitable phenylalkanoic acid followed by reduction of the nitro group. For example, 2,3,5,6-tetrafluorophenylacetic acid is converted to 4-amino-2,3,5,6-tetrafluorophenylacetic acid by this method. The [4-amino-(mono- or poly-fluoro)benzoyl]alkanoic acids and esters are prepared by the reaction of ammonia or sodium amide with (4-halobenzoyl)alkanoic acids. For example, the reaction of sodium amide with ethyl 2,3,4,5,6-pentafluorobenzoylacetate yields ethyl(4-amino-2,3,5,6-tetrafluorobenzoyl)acetate.

Many of the novel 4-(monosubstituted-amino)phenyl compounds of the present invention may be prepared by reaction of the appropriate 4-aminophenyl compound with a suitable alkylating agent such as an alkyl halide, sulfate, tosylate, or trifluoromethanesulfonate with or without a solvent at 30° C. to 150° C. Appropriate 4-aminophenyl compounds are, for example, ethyl 4-amino-2-fluorobenzoate; ethyl 4-amino-3-fluorobenzoate; 2,3-dihydroxypropyl 4-amino-3-fluorobenzoate; phenyl 2-fluorobenzoate; 1-(4-amino-3-fluorobenzoyl)-pyrrolidine; and ethyl 4-(4-amino-2-fluorophenyl)butyrate. Suitable solvents are lower alkanols, N,N-dimethylformamide, N,N-dimethylacetamide, 1,2-dimethoxyethane, acetonitrile, toluene, benzene, hexamethylphosphoramide and the like. The reaction may be carried out with two equivalents of the 4-aminophenyl compound or with one equivalent of the compound plus one equivalent of a base such as an alkali carbonate or bicarbonate or an unreactive organic base such as diisopropylethylamine or alternatively with a catalytic amount of copper powder when a alkyl halide is used as the alkylating agent. Similarly, alkylation of the sodium salt (formed with sodium hydride) of either the amino group of a 4-aminophenyl compound or the anilide moiety of a 4-(acetylamino)phenyl compound yields the novel 4-(monosubstituted-amino)phenyl compounds or an N-acetyl derivative thereof. Removal of the N-acetyl group by conventional hydrolytic methods affords the desired 4-(monosubstituted amino)phenyl compounds.

Alternative methods of preparation of these compounds are by reactive alkylation of a 4-aminophenyl compound, which may be generated in situ by reduction of a 4-aminophenyl precursor such as a 4-nitrophenyl compound and the like or by a metal hydride reduction of a 4-(acylamino)phenyl compound. For example, n-hexadecanal or another carbonylalkane and 4-amino-2-fluorobenzoic acid are reduced under 1–10 atmospheres of hydrogen using an activated metal catalyst or with a metal hydride such as sodium borohydride forming 4-(hexadecylamino)-2-fluorobenzoic acid and the like. Diborane reduction of 4-(alkanoylamino)phenyl compounds such as ethyl 4-(hexadecanoylamino)-3-fluorobenzoate at room temperature or above for 1–6 hours yields the corresponding 4-(alkylamino)phenyl compounds such as ethyl 4-(hexadecylamino)-3-fluorobenzoate. The 4-(alkanoylamino)phenyl compounds used in these reductions are prepared by acylation of the appropriate 4-aminophenyl compounds with suitable acylating agents, such as alkanoyl halides. To prepare the ring-fluorinated 4-(alkylamino)phenyl alkenoic and alkynoic acids it is advantageous to form the corresponding ring-fluorinated alkylchloroimide from the 4-(alkanoylamino)phenyl compounds using phosphorus oxychloride and base, and then reduce the alkylchloroimide moiety to an alkylamino group with sodium borohydride.

A method particularly useful for the introduction of the monosubstituted-amino group into polyfluorinated aromatic compounds is nucleophilic aromatic substitution. An example of this method is the reaction of hexadecylamine (or the anion derived therefrom by treatment with a strong base) with ethyl pentafluorobenzoate to yield ethyl 4-(hexadecylamino)-2,3,5,6-tetrafluorobenzoate. In certain instances an amine such as hexadecylamine may be reacted with a benzyne such as that derived from ethyl 4-bromo-3-fluorobenzoate by treatment with sodium amide to yield the 4-(mono-substituted-amino)phenyl compound, in this case ethyl 3-fluoro-4-(hexadecylamino)benzoate.

The 4-(monosubstituted-amino)benzoic, benzoylalkanoic, and phenylalkanoic and acids of this invention are often prepared from the corresponding p-aminobenzoic, benzoylalkanoic, and phenylalkanoic and acids by the sequence involving esterification of the amino acid with ethanol in the presence of boron trifluoride etherate, followed by alkylation of the amino function by the methods above. the free acids are then liberated by hydrolysis of the ester with aqueous alcoholic sodium hydroxide at 80° for 2–10 hours followed by acidification. The acids obtained by this procedure may be converted to the corresponding metallic cationic salts. For example, the sodium salt may be prepared by reaction of the acid with sodium hydroxide in a mixture of ethanol and water.

Alternatively, the acids of this invention may be prepared by hydrolysis of the corresponding nitriles or various amides, imidates or oxazolines. The carboxylic acid moiety may also be generated by oxidation of the corresponding aldehydes, acetophenones, benzyl alcohols, or toluenes, most often with the use of an amine-protecting group such as trifluoroacetyl or t-butyloxycarbonyl.

The carboxaldehydes of this invention may be prepared by several methods among which is alkylation of the corresponding acetal by the methods above followed by hydrolysis of the resulting 4-(monosubstituted-amino)phenyl acetal to the desired aldehyde. Aldehydes may also be prepared by reduction of the appropriate nitriles. For example, treatment of 3-fluoro-4-(hexadecylamino)hydrocinnamonitrile with stannic chloride and anhydrous hydrogen chloride gas, followed by hydrolysis in hot water provides 3-fluoro-4-(hexadecylamino)hydrocinnamaldehyde. These reductions are also conveniently carried out with hydrides such as diisobutyl aluminum hydride.

The novel esters and amides of the present invention may readily be prepared by treating a derivative of the corresponding carboxylic acid, such as the acid halide, mixed acid anhydride or activated ester or amide with the appropriate alcohol or amine, respectively. These reactions may be carried out in an inert solvent at a temperature of 50°–125° C. for 30 minutes to 18 hours or more. In the case of the acid halide and other acid-forming acylating agents, the reaction is carried out in the presence of an acid scavenger such as diisopropylethylamine; 4-dimethylaminopyridine; pyridine; triethylamine; finely powdered sodium carbonate and the like. A protecting group on the amino nitrogen is used for best results. The simplest protecting group is provided by protonation of the amine to yield an anilinium salt prior to or during formation of the acylating form of the carboxyl group. Acylation of the amino group by carefully selected acyl groups such as carbobenzyloxy, carbo-t-butoxy, and trifluoroacetyl provides protection of this group from self-acylation during amide or ester formation. These protecting groups are then removed by catalytic hydrogenation, mild acid treatment, and mild alkali treatment, respectively. Other N-acyl protecting groups such as acetyl and succinoyl may be used and these are removed by conventional methods. Activated esters and amides, useful to synthesize the esters and amides of the present invention, are those containing carboxymethyl, 4-nitrophenyl, N-oxysuccinimide and 1-imidazolyl groups and the like. In certain cases, treatment of the acids with an excess of an appropriate hydroxy-containing substrate in the presence of a Lewis or mineral acid such as boron trifluoride, sulfuric acid or hydrochloric acid affords the corresponding esters. Ordinary esters such as the methyl and ethyl esters are sufficiently reactive to form the amides of the 4-(monosubstituted-amino)benzoic acids and highly reactive amine substrates such as hydroxylamine, hydrazines and certain alkyl primary amines. With certain kinds of substrates in order to form amides it is necessary to first form the alkali metal or strong organic base salts of these substrates prior to reacting them with the various aforementioned acylating forms of the 4-(monosubstituted-amino)benzoic acids. E.g., the aminoalkanecarboxylic and aminoalkanesulfonic acids are Zwitterionic and must be converted to their salts, suitably in situ. They may also be used in the form of their esters and then hydrolyzed after amide formation. Certain substrates which are neutral, like the carboxamides, or slightly acidic, like the alkane or arene sulfonamides, are converted to reactive sodium salts by reaction with sodium hydride or other basic reagents.

The α-substituted ring-fluorinated 4-(monosubstituted-amino)acetophenones of the invention are prepared by reaction of a derivative of the appropriate benzoic acid, such as 2-fluoro-4-(hexadecylamino)benzoyl chloride hydrochloride, with two or more equivalents of the reactive salt of an acidic methylene compound, for example the sodium salt of diethyl malonate. Other benzoic acid derivatives are also suitable for this reaction, such as a ring-fluorinated 4-[N-trifluoroacetyl(-monosubstituted)amino]benzoyl chloride, a ring-fluorinated 4-[N-tert-butyloxycarbonyl(monosubstituted)amino]benzoyl chloride or a ring-fluorinated methyl 4-(monosubstituted-amino)benzoate ester. In some cases the final step in the preparation of the α-substituted 4-(monosubstituted-amino)acetophenones is the removal of the nitrogen protecting group. In other cases, hydrolysis of one or more of the ester groups in the acylation product affords an unstable polycarboxlic acid which undergoes decarboxylation to allow the preparation of another acetophenone derivative. For example, the reaction of tert-butyl ethyl [3-fluoro-4-(hexadecylamino)benzoyl]malonate with trifluoroacetic acid affords ethyl 3-fluoro-4-(hexadecylaminobenzoyl)acetate. In other cases, hydrolysis of one or more of the ester groups allows the preparation of the corresponding acid derivative. For example, the hydrolysis of ethyl [3-fluoro-4-(hexadecylamino)benzoyl]acetate yields [3-fluoro-4-(hexadecylamino)benzoyl]acetic acid.

An alternative procedure for preparing certain ring-fluorinated α-substituted-4-(monosubstituted-amino)acetophenones is alkylation of the corresponding 4-aminoacetophenone by the methods above. For example, alkylation of methyl 3-(3-fluoro-4-aminobenzoyl)propionate with hexadecyl bromide yields methyl 3-[3-fluoro-4-(hexadecylamino)benzoyl]propionate. The related carboxylic acids are then obtained by hydrolysis. Certain of these acids are particularly useul for the preparation of ring fluorinated [4-(monosubstituted-amino)phenyl]alkanoic acids by reduction. For example, the Clemmensen or Wolff-Kishner reduction of 3-[3-fluoro-4-(hexadecylamino)benzoyl]propionic acid yields 4-[3-fluoro-4-(hexadecylamino)phenyl]butyric acid.

The ring-fluorinated 4-aminophenylalkenoic acids or [4-(monosubstituted-amino)phenyl]alkenoic acids may be prepared by condensation of the appropriate aldehydes or by dehydration of the corresponding substituted phenyl-hydroxyalkanoic acids. For example, ethyl 5-[2-fluoro-4-(hexadecylamino)phenyl]-2,4-pentadienoate is obtained by the Wittig reaction of 2-fluoro-4-(hexadecylamino)benzaldehyde with the Wittig reagent, ethyl 4-(triethylphosphono)crotonate. Alternatively, these alkenoic acids are obtained by heating 4-(N-decyl-N-[methyl or acetyl]amino)-3-fluorobenzaldehyde and the like with the sodium salt of the carbanion of ethyl acetate or with a mixture of ethyl acetate, acetic anhydride and potassium acetate. The second method is illustrated by dehydration of ethyl 3-[(4-alkylamino-2-fluoro)phenyl]-3-hydroxypropionate to yield ethyl 3-(4-alkylamino-2-fluoro)cinnamate.

The acetylenic analogs are prepared by dehydrobromination of the side chain vic-dibrominated alkanoic acid. For example dehydrobromination of ethyl 3-[(4-alkylamino-2-fluoro)phenyl]-2,3-dibromopropionate, its isomers or N-acyl analogs or of ethyl 3-[(4-alkylamino-2-fluoro)phenyl]-3-bromoacrylate yields ethyl 3-(4- alkylamino-2-fluoro)phenylpropiolate. The acetylenic acids are also formed from (4-alkylamino-2-fluoro)phenylacetylene metal salts by carboxylation with carbon dioxide. The (4-alkylamino-2-fluoro)phenylacetylenes are also used by N-acylating with t-butyl azidoformate followed by conversion to the lithium acetylide salt and subsequent reaction of the lithium salt with boron trifluoride etherate in tetrahydrofuran at $-20°$ C. to form tris-[(4-alkylamino-2-fluoro)phenylethynyl]boranes. The tetrahydrofuran solution of the borane is in turn reacted with ethyl diazoacetate, followed by water to yield ethyl 4-[(4-alkylamino-2-fluoro)-phenyl]butynoate.

The ring-fluorinated 4-(alkylamino)phenylalkanoic acids, amides, or esters are also prepared by catalytic reduction at 1 to 10 atmospheres of hydrogen of the corresponding alkenoic or alkynonic derivatives.

The ring-fluorinated 4-(substituted-amino)phenyl alkenoic acids and derivatives are prepared by Friedel-Crafts acylation of the N-acyl-N-alkylanilines with the appropriate dicarboxylic acid anhydride or half acid chloride. The 4-(substituted-amino)benzoylalkanoic acids or esters, obtained by this and by other syntheses, may be converted to the 4-(substituted-amino)-phenylalkanoic acids by reduction with (a) hydrazide and alkali in diethylene glycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of the 4-(substituted-amino)phenylalkanoic acids are prepared by heating the corresponding 4-(substituted-amino)phenyl alkyl ketones with aqueous alcoholic ammonium polysulfide followed by hydrolysis to yield the acids with the same number of carbon atoms as the ketone. These acids are also prepared by reacting 4-(N-t-butyloxy-carbonyl-N-substituted-amino)phenylmagnesium halides with 2-(3-halopropyl)-2-oxazolines, follow-ed by mild acid removal of 2-oxazolinyl and t-butoxycarbonyl protecting groups. Similarly, the above Grignard reagent can be reacted with 3-bromotriethylorthopropionate in the presence of dilithiumtetrachlorocuprate to yield the desired acids after removal of the protecting groups from the amino and carboxyl groups.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.35 gram to about 7.0 grams of the active compound, for a subject of about 70 kg. of body weight, are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or to otherwise modify the physical form of the dosage unit. For instance, tablets, pills or capsules may be coatd with shellac, sugar or both. A syrup or elixir may contain the active compound, sucrose as a sweetening agent, methyl and propyl parabens as preservatives, a dye, and flavoring such as cherry or orange flavor. Of course, any material used in preparing any dosage unit form should be pharmaceutically pure and substantially non-toxic in the amounts employed. In addition, the active ingredients may be incorporated into sustained-release preparations and formulations.

The invention will be described in greater detail in conjunction with the following specific Examples.

EXAMPLES 1. 3-Fluoro-4-methylacetanilide

To a solution of 22.1 g of 3-fluoro-4-methylaniline in 200 ml of ethyl ether is added 19.5 ml (21.1 g) of acetic anhydride at such a rate as to maintain gentle reflux. When the addition is complete, the solution is stirred for another 15 minutes, then heated to reflux for 1 hour. The mixture is then concentrated and upon cooling a solid is obtained. Recrystallization from chloroform hexane yields 3-fluoro-4-methylacetanilide as white solid.

2. 4-Acetamido-2-fluorobenzoic acid

Solid 3-fluoro-4-methyl acetanilide (10.0 g) is slowly added to a solution of 29.4 g potassium permanganate and 20.4 g. magnesium sulfate in 1.0 l of water at 65° C. After the addition is complete, the mixture is heated under reflux for 6 hours, cooled and allowed to stand overnight. Solid sodium carbonate (29.0 g.) is then added, the reaction mixture is stirred for 15 minutes and filtered. The colorless filtrate is then acidified with 40 ml of concentrated hydrochloric acid and chilled. Filtration yields a white solid. Recrystallization from ethanol-water provides 4-acetamido-2-fluorobenzoic acid.

3. Ethyl 4-amino-2-fluorobenzoate

A solution of 10.0 g of 4-acetamido-2-fluorobenzoic acid, 100 ml of ethyl alcohol and 2.0 ml of boron trifluoride etherate is heated under reflux for 22 hours. The solvent is slowly removed by distillation as an equal amount of fresh ethyl alcohol is added. After 200 ml of solvent has been removed, the remainder is evaporated at reduced pressure. The residue is dissolved in ethyl acetate, washed with saturated aqueous sodium bicarbonate, dried and the solvent then evaporated to yield a solid. Recrystallization of the solid from ethanol-hexane yields ethyl 4-amino-2-fluorobenzoate.

4. Ethyl 2-fluoro-4-(hexadecylamino)benzoate

A mixture of 2.6 g of ethyl 4-amino-2-fluorobenzoate 4.5 g of hexadecylbromide, 2.0 g of anhydrous potassium carbonate and 20 ml of hexamethylphosphoramide is heated to 130° C. for 22 hours. The mixture is cooled, diluted with 200 ml of water, and extracted twice with ethyl ether. The combined extracts are washed with water, dried, and the ether evaporated and the residue upon recrystallization from hexane yields ethyl-2-fluoro-4-(hexadecylamino)benzoate as a white solid.

5. Methyl 2-fluoro-4-(hexadecylamino)benzoate

A mixture of 8.3 g. of methyl 4-amino-2-fluorobenzoate, 15.0 g of hexadecylbromide, 6.8 g of anhydrous potassium carbonate and 50 ml of hexamethylphosphoramide is heated to 135° for 20 hours. Upon cooling, dilution with water and extraction with ether, the orange colored ethereal extract is washed with water, dried and evaporated to yield an off-white solid. Recrystallization of this material from hexane affords methyl-2-fluoro-4-(hexadecylamino)benzoate.

6. 2-Fluoro-4-(hexadecylamino)benzoic acid

A mixture of 3.5 g of methyl 2-fluoro-4-hexadecylaminobenzoate, 40 ml of ethanol, 60 ml of water, and 3.8 g of potassium hydroxide is heated on a steam bath for 14 hours. The hot solution is acidified with concentrated hydrochloric acid. The reaction mixture is cooled and filtered. The colorless residue is recrystallized from chloroform-hexane to yield 2-fluoro-4-(hexadecylamino)benzoic acid as a white solid.

7. Sodium 2-fluoro-4-(hexadecylamino)benzoate

A mixture of 3.62 g. of 2-fluoro-4-(hexadecylamino)benzoic acid and 25 ml of ethanol-water (9:1) containing 0.400 g of sodium hydroxide is stirred for 4 hours. The mixture is filtered and the residue washed with 10 ml of ethanol-water (9:1) and dried, in vacuo, over $P_2O_5$ for 24 hours to yield sodium 2-fluoro-4-(hexadecylamino) benzoate as a white solid.

8. Ethyl 4-amino-3-fluorobenzoate

A solution of 15.0 g of 4-amino-3-fluorobenzoic acid 150 ml of anhydrous ethyl alcohol and 5 ml of boron trifluoride etherate is heated to reflux for 20 hours. Most of the solvent is then removed and 200 ml of water added and the mixture extracted with chloroform. The chloroform extract is washed with an aqueous solution of sodium bicarbonate dried over sodium sulfate and the solvent evaporated to yield an off-white solid which upon recrystallization from ethanolhexane yields ethyl 4-amino-3-fluorobenzoate as a white solid.

9. Ethyl 3-fluoro-4-(hexadecylamino)benzoate

A mixture of 4.0 g of ethyl 4-amino-3-fluorobenzoate, 6.66 g of hexadecyl bromide and 3.0 g of potassium carbonate in 25 ml of hexamethyl phosphoramide is stirred at 150° C. for 20 hr. The mixture is cooled, diluted with water and extracted with ether. The ether extract is washed with water, dried, and the ether evaporated. The residue is recrystallized from hexane to yield ethyl 3-fluoro-4-(hexadecylamino)benzoate as a white solid.

10. 3-Fluoro-4-(hexadecylamino)benzoic acid

A solution of 3.8 g of potassium hydroxide in 15 ml of water is added to a mixture of 3.5 g of ethyl 3-fluoro-4-hexadecylaminobenzoate, 30 ml of water and 30 ml of ethanol. Upon heating, a clear solution is formed and after 20 hours, the hot solution is acidified with concentrated hydrochloric acid and cooled. The precipitate is collected and recrystallized from ethanol and then from chloroform to yield 3-fluoro-4-(hexadecylamino)benzoic acid as a colorless solid.

11. Ethyl 2-fluoro-4-(octylamino)benzoate

A mixture of 33 g of ethyl 4-amino-2-fluorobenzoate, 44 ml of 1-bromooctane and 0.50 g of copper powder is heated on a steam bath for 19 hours. The mixture is chilled, diluted with ethanol, filtered and the solid washed with cold ethanol and with water to give tan crystals. The filtrate is neutralized with 10 N potassium hydroxide, chilled and filtered and the solid washed with water and with ethanol to give tan crystals. The two crops of crystals are combined and recrystallized from ethanol to yield ethyl 2-fluoro-4-(octylamino)benzoate as a white solid.

12. Ethyl 3-fluoro-4-(tetradecylamino)benzoate

To a solution of 16.5 g of ethyl 3-fluorobenzoate in 150 ml. of dry N,N-dimethylformamide is added 4.12 g of sodium hydride (56% in oil) and 27.7 g of 1-bromotetradecane. The mixture is heated on a steam bath until hydrogen evolution began and then chilled briefly to control the reaction. After the sodium hydride has reacted, the mixture is heated on a steam bath under nitrogen for 6 hours. The mixture is chilled, filtered and the solid washed with ethanol and with water to give ethyl 3-fluoro-4-(tetradecylamino)benzoate.

13. Ethyl 4-(p-chlorobenzylamino)-2-fluorobenzoate

Ethyl 4-amino-2-fluorobenzoate (17 g), 4-chlorobenzaldehyde (14 g), and 100 ml of absolute alcohol are heated on a steam bath for 10 minutes. Upon cooling, the mixture is filtered. The residue is dried and then dissolved in 200 ml of hot ethanol and 4 g of sodium borohydride is added in portions with stirring. The mixture is then heated under reflux, with stirring, for 3 hours, cooled, added to ice water and filtered to yield ethyl 4-(p-chlorobenzylamino)-2-fluorobenzoate as a solid.

14. Ethyl 3-fluoro-4-(hexadecanoylamino)benzoate

A solution of hexadecanoyl chloride (20 g) in 100 ml of methylene chloride is slowly added with stirring to a solution of 20 g of ethyl 4-amino-3-fluorobenzoate in 100 ml of methylene chloride. The mixture is filtered and the filtrate is washed with dilute hydrochloric acid and water, dried and the solvent evaporated. Crystallization of the residue from acetonitrile affords ethyl 3-fluoro-4-(hexadecanoylamino)benzoate.

15. Ethyl 3-fluoro-4-(hexadecylamino)benzoate

A solution of 5 g of ethyl 3-fluoro-4-(hexadecanoylamino)benzoate in 50 ml of tetrahydrofuran is slowly added with stirring to 13 ml of 1 M borane in tetrahydrofuran. The resulting solution is then poured into 50 ml of 10% aqueous hydrochloric acid and the resulting mixture is filtered. The residue is crystallized from acetonitrile to yield ethyl 3-fluoro-4-(hexadecylamino)benzoate as white crystals.

16. 4-Amino-2,3,5,6-tetrafluorobenzoic acid

A mixture of 10.0 g of 2,3,4,5,6-pentafluorobenzoic acid and 400 ml of nitromethane is saturated with anhydrous ammonia at room temperature and then placed in a bomb and heated at 100° for 20 hrs. The resulting solution is evaporated and the residue crystallized from chloroform-hexane to yield 4-amino-2,3,5,6-tetrafluorobenzoic acid as a white solid.

17. 4,14-Pentadecadienyl methanesulfonate

To a solution of 4,14-pentadecadien-1-ol (15.0 g) and triethylamine (14 ml.) in dry methylene chloride (320 ml.) at −8° C. is added methanesulfonylchloride (5.73 ml.), dropwise. The reaction mixture is stirred at −10° C. for 30 minutes and then diluted with methylene chloride, extracted with ice-water (250 ml.), followed by cold 10% HCl (200 ml.); cold saturated sodium bicarbonate (200 ml.) and cold brine (200 ml.). The organic phase is dried (MgSO$_4$) and the solvent removed in vacuo to provide 4,14-pentadecadien-1-yl methanesulfonate as a clear oil.

18. Ethyl 2-fluoro-4-[(4,14-pentadecadienyl)amino]benzoate

A solution of 18.1 g. of 4,14-pentadecadien-1-yl-methanesulfonate, as prepared in Example 17 above and 19.8 g. of ethyl p-aminobenzoate in hexamethylphosphoramide is heated at 120° C. for 20 hours. After cooling, the reaction mixture is diluted with ethanol:water (1:1) (30 ml.) and chilled. More ethanol is added, the mixture is filtered and solid residue is recrystallized from ethanol to yield ethyl 2-fluoro-4-[(4,14-penadecadienyl)amino]benzoate as a white solid.

TABLE I

The following benzoic acids are prepared from the corresponding ethyl esters by the hydrolysis procedure of Example 6. The requisite esters are obtained by the reaction of the appropriate alkyl halide or mesylate with the appropriate ring-substituted ethyl 4-aminobenzoate by the methods of Examples 4 and 18.

| Example No. | Compound |
| --- | --- |
| 19 | 3,5-Difluoro-4-(hexadecylamino)benzoic acid |
| 20 | 4-(Hexadecylamino)-2,3,5-trifluoro benzoic acid |
| 21 | 4-(Hexadecylamino)-2,3,5,6-tetrafluorobenzoic acid |
| 22 | 4-(Hexadecylamino)-2-methylbenzoic acid |
| 23 | 2-Chloro-4-(tetradecylamino)benzoic acid |
| 24 | 3,5-Dibromo-4-(undecylamino)benzoic acid |
| 25 | 3-Fluoro-4-(octadecylamino)benzoic acid |
| 26 | 2-Fluoro-4-(1-methylpentadecylamino)benzoic acid |
| 27 | 3-Bromo-4-(1-ethyltetradecylamino)benzoic acid |
| 28 | 2-Methoxy-4-(6-methylhexadecylamino)benzoic acid |
| 29 | 2-Fluoro-4-(14-methylpentadecylamino)benzoic acid |
| 30 | 3,5-Diiodo-4-(15-methylhexadecylamino)benzoic acid |
| 31 | 3-Chloro-4-(3,7,11-trimethyldodecylamino)benzoic acid |
| 32 | 2-Methoxy-4-(3,7,11,15-tetramethylhexadecylamino)-benzoic acid |
| 33 | 2-Fluoro-4-(13,13-dimethyltetradecylamino)benzoic acid |
| 34 | 3,5-Dimethyl-4-(15,15-dimethylhexadecylamino) benzoic acid |
| 35 | 2-Hydroxy-4-(10-undecenylamino)benzoic acid |
| 36 | 3-Methyl-4-(4-hexadecenylamino)benzoic acid |
| 37 | 2-Fluoro-4-(2,6,10-trimethyl-11-dodecenylamino)-benzoic acid |
| 38 | 3,5-Difluoro-4-(9-octadecenylamino)benzoic acid |
| 39 | 3-Nitro-4-(3,7-dimethyl-6-0ctenylamino)benzoic acid |
| 40 | 3,5-Dichloro-4-(1-methyl-6-heptenylamino)benzoic acid |
| 41 | 3-Fluoro-4-(4,14-pentadecadienylamino)benzoic acid |
| 42 | 2-Fluoro-4-(3,7,11-trimethyl-2,6,10-dodecatrienyl-amino)benzoic acid |
| 43 | 2,6-Difluoro-4-(11-hexadecynylamino)benzoic acid |
| 44 | 3,5-Dibromo-4-(6-methyl-6-hepten-2-ynylamino) benzoic acid |
| 45 | 2-Methyl-4-[3-(1,3-dimethylcyclohexyl-2-propyl)-amino]benzoic acid |
| 46 | 2-Methoxy-4-(13-cyclopentyltridecylamino)benzoic acid |
| 47 | 2-Fluoro-4-(11-cyclohexylundecylamino)benzoic acid |
| 48 | 3-Fluoro-4-cyclotetradecylaminobenzoic acid |
| 49 | 2-Chloro-4-[4-(1-cyclohexenyl)butylamino]benzoic acid |
| 50 | 2,6-Difluoro-4-[(4-cyclohexyl-2-butenyl)amino]-benzoic acid |
| 51 | 2-Fluoro-4-(11-phenylundecylamino)benzoic acid |
| 52 | 3-Fluoro-4-(4-chlorobenzylamino)benzoic acid |
| 53 | 2-Methyl-4-[2-(4-fluorophenyl)ethylamino]benzoic acid |
| 54 | 2-Acetoxy-4-(4-decyloxybenzylamino)benzoic acid |
| 55 | 3-Fluoro-4-(4-methylbenzylamino)benzoic acid |
| 59 | 3-Methyl-4-[6-(2-furyl)hexylamino]benzoic acid |
| 60 | 3-Bromo-4-[3-(2,4-dichlorophenyl)propylamino] benzoic acid |
| 61 | 2-Fluoro-4-[3-(4-benzyloxyphenyl)propylamino] benzoic acid |
| 62 | 3-Fluoro-4-[2-(1-naphthyl)ethylamino]benzoic acid |
| 63 | 2,5-Difluoro-4-(hexadecylamino)benzoic acid |
| 64 | 2-Fluoro-4-(tetradecylamino)benzoic acid |
| 65 | 3-Fluoro-4-(undec-10-enylamino)benzoic acid |
| 66 | 2-Fluoro-4-(hexadecylamino)benzaldehyde |

2-Fluoro-4-aminobenzonitrile (11.8 g) and 1-bromohexadecane (15.3 g) are dissolved in hexamethylphosphoramide (200 ml.) and heated under an atmosphere of nitrogen in an oil bath maintained at 120° C. for 22 hours. The reaction mixture is cooled to room temperature and water is added gradually. The mixture is then chilled in an ice-bath and filtered. The solid is washed thoroughly with water and dried. The solid is recrystalllized from ether-hexane to yield 2-fluoro-4-(hexadecylamino)benzonitrile as a pale yellow solid.

Di-isobutylaluminum hydride (54 ml., 25% solution in toluene) is added with stirring to a solution of the 2-fluoro-4-(hexadecylamino)benzonitrile under a nitrogen atmosphere. The temperature rises to 40° C. during the addition which takes 30 minutes and the reaction is then stirred for 1 hour. A solution of methanol in toluene (50 ml., 1:1) is added during 30 minutes and the mixture is poured into vigorously stirred ice-cold aqueous sulfuric acid (500 ml., 5%). After 10 minutes, diatomaceous earth (30 g.) is added, the mixture filtered and the organic layer separated. The aqueous solution is extracted twice with toluene (100 ml.) and the combined organic layers are washed with aqueous sodium bicarbonate, dried over magnesium sulfate, decolorized with charcoal, filtered and evaporated in vacuo to give a light yellow crystalline solid. Recrystallization from hexane affords 2-fluoro-4-(hexadecylamino)benzaldehyde as a white solid.

67. 3-Fluoro-4-(hexadecylamino)acetophenone

3-Fluoro-4-aminoacetophenone (87.6 g.) is heated with 1-bromohexadecane (198 g.) in dry hexamethylphosphoramide (300 ml.) containing potassium carbonate (90 g.) for 16 hours at 100° C. The solution is cooled to room temperature, filtered to remove solids, and the filtrate is dilulted with cold water (20 ml.). The amber solid so obtained is collected and washed with water. Recrystallization of the solid from ethanol and then from dichloromethane affords 3-fluoro-4-(hexadecylamino)acetophenone.

68. 2-[2-Fluoro-4-(hexadecylamino)phenyl]1,3-dioxolane

2-Fluoro-4-(hexadecylamino)benzaldehyde (1.7 g.) is dissolved in toluene (20 ml), and ethylene glycol (2.5 ml.) and p-toluenesulfonic acid (10 mg.) are added. The reaction mixture is heated under reflux for 16 hours while water is removed using a Dean-Stark trap. The reaction mixture is then cooled to room temperature, diluted with toluene (70 ml.), washed with aqueous sodium bicarbonate and then with water. The organic layer is separated dried over mangnesium sulfate, decolorized with charcoal and filtered through anhydrous magnesium silicate. Removal of the solvent in vacuo gives a light yellow solid which is recrystallized from hexane to yield 2-[2-fluoro-4-(hexadecylamino)phenyl]-1,3-dioxolane.

69. 3-fluoro-4-(hexadecylamino)benzoyl chloride hydrochloride

A cold solution of 25 g. 3-fluoro-4-(hexadecylamino)-benzoic acid in 500 ml. dimethoxyethane-methylene chloride (4:1) is prepared and dry hydrochloric acid is bubbled through the solution until no more precipitate forms. The solution is treated with 25 ml. thionyl chloride and refluxed until all of the precipitate has dissolved. The solvents are evaporated to yield 3-fluoro-4-4-(hexadecylamino)benzoyl chloride hydrochloride as an orange, semi-crystalline mass.

70. N-Trifluoroacetyl-3-fluoro-4-(hexadecylamino)benzoyl chloride

A stirred, ice-cold suspension of 9 g. 3-fluoro-4-(hexadecylamino)benzoic acid in 100 ml. of dimethoxyethane and 16 ml. of pyridine is treated with 18 ml. trifluoroacetic anhydride at 0° C. The solution is stirred at 0° C. for 30 minutes at room temperature and then diluted with 300 ml. ether and 100 g. ice. After stirring vigorously for 15 minutes, the phases are separated, the ether solution is washed with brine, dried and evaporated to a white, amorphous solid.

To a solution of 9.2 g. of the above solid in 30 ml. methylene chloride and 0.5 ml. dimethylformamide is added 5.7 ml. thionyl chloride. After 20 hours at reflux, the solvents are evaporated to yield N-trifluoroacetyl-3-fluoro-4-(hexadecylamino)benzoyl chloride as a light yellow, mobile oil.

71. N-Carbobenzyloxy-2-fluoro-4-(hexadecylamino)benzoyl chloride

To 15 g. 2-fluoro-4-(hexadecylamino)benzoic acid in 200 ml. warm chloroform is added a solution of 15 g. of sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time, ultimately to yield N-carbobenzyloxy-2-fluoro-4-(hexadecylamino)benzoyl chloride as a viscous, orange oil.

72. 4-(N-tert-Butyloxycarbonyl-N-hexadecylamino)-3-fluorobenzoyl imidazole

A solution of 10 g. 3-fluoro-4-(hexadecylamino)benzoic acid in 100 ml. dioxane is treated with 4.0 g. tert-butylazidoformate and 10 ml pyridine. After stirring at room temperature for 18 hours, the protected amino-acid is precipitated from solution by the addition of 150 ml. water. The solid is collected, and thoroughly dried, and dissolved in 200 ml. of a mixture consisting of methylene chloride/dimethoxyethane/pyridine (1:4:1). To this solution is added 5.4 g. 1,1'-carbonyldiimidazole. The solution is stirred overnight at room temperature and the solvents are evaporated to yield 4-(N-tert-butyloxycarbonyl-N-hexadecylamino)-3-fluorobenzoylimidazole as an orange oil.

73. 2,3-Dihydroxypropyl 2-fluoro-4-(hexadecylamino)benzoate

A solution of 7.34 g. of 2-fluoro-4-(hexadecylamino)-benzoic acid, 4.80 g. of 25% aqueous sodium hydroxide, and 12.6 g. of 3-iodo-1,2-propanediol in 50 ml of hexamethylphosphoramide is stirred for 24 hours at ambient temperature, diluted with 100 ml of ether and stirred for 5 days at ambient temperature. The mixture is treated with water and extracted with ether. The dried extracts are evaporated to yield 2,3-dihydroxypropyl 2-fluoro-4-(hexadecylamino)benzoate.

74. Methyl 3-fluoro-4-(hexadecylamine)benzoate

A solution of 7.20 g of 3-fluoro-4-(hexadecylamino)-benzoic acid in 25 ml of hexamethylphosphoramide is added to a stirred mixture of 0.800 g of sodium hydride (57% in mineral oil) and 25 ml of hexamethylphosphoramide. The solution which forms after one hour is treated with 11.0 g of methyl iodide and is then stirred at 25° C. for 18 hours Dilution with water followed by filtration affords a white solid which is crystallized from ethanol to yield methyl 3-fluoro-4-(hexadecylamino)-benzoate as a white solid.

75. 3-Hydroxypropyl 3-fluoro-4-hexadecylamino)benzoate

A mixture of 2.25 g of methyl 3-fluoro-4-(hexadecylamino)benzoate, 280 mg of 1,3-propanediol and 1.37 g. of p-toluenesulfonic acid is heated at 180° C. for 18 hours and then is partitioned between ether and 3% aqueous sodium carbonate solution. The ether layer is separated, dried, and evaporated to yield 3-hydroxypropyl 3-fluoro-4-(hexadecylamino)benzoate.

76. 2-Ethoxyethyl 2-fluoro-4-(hexadecylamino)benzoate

A solution of 11.8 g of 2-fluoro-4-(hexadecylamino)-benzoic acid, 1.00 g. of 2-ethoxyethanol and 5.35 ml of boron trifluoride etherate in 200 ml of toluene is stirred under reflux for 48 hours. The solution is treated with an additional 5.35 ml of boron trifluoride etherate and refluxing is continued for 120 hours. Dilution with water and methylene chloride followed by filtration affords 2-ethoxyethyl 2-fluoro-4-(hexadecylamino)benzoate as a white solid.

77. Methyl 2-fluoro-4-(hexadecylamino)benzoate

A solution of 50.5 g of 2-fluoro-4-(hexadecylamino)-benzoic acid and 34.4 ml of boron trifluoride etherate in 200 ml of methanol is stirred under reflux for 44 hours, allowed to cool, and poured into 1.20 liters of ice cold 5% aqueous sodium carbonate solution. The white solid is collected by filtration and recrystallized from benzene-ethanol to yield methyl 2-fluoro-4-(hexadecylamino)benzoate.

78. 1-(Methoxycarbonyl)propyl 3-fluoro-4-(hexadecylamino)benzoate

To a solution of 10.0 g 3-fluoro-4-(hexadecylamino)-benzoyl chloride hydrochloride in 200 ml methylene chloride is added dropwise a solution of 3 g. methyl α-hydroxybutyrate and 5 g triethylamine in 100 ml. ether. After 17 hours stirring at room temperature, the precipitate is collected and washed with several portions of ether. The ether solution is washed with water, dried and evaporated to yield 1-(methoxycarbonyl)propyl 3-fluoro-4-(hexadecylamino)benzoate as a white solid.

79. 1-(Ethoxycarbonyl)ethyl 3-fluoro-4-(hexadecylamino)benzoate

To a warm mixture of 7 g sodium 3-fluoro-4-(hexadecylamino)benzoate in 100 ml. ethanol is added 4.7 g. ethyl α-tosyloxypropionate. After 17 hours at reflux, the cooled solution is diluted with an equal volume of water and the resultant precipitate is filtered. After washing with cold ethanol and drying, the product is crystallized from acetonitrile to yield 1-(ethoxycarbonyl)ethyl 3-fluoro-4-(hexadecylamino)benzoate as colorless crystals.

80. 1-Carboxyethyl 2-fluoro-4-(hexadecylamino)benzoate

A flask containing 10.0 g 2-fluoro-4-(hexadecylamino)benzoic acid, 3.3 g. lactic acid, 500 mg. toluenesulfonic acid and 500 ml. toluene is equipped with a Soxhlet extractor charged with activated 4 A Linde molecular sieves. The solution is refluxed for 24 hours, during which time the Soxhlet extractor is charged twice more with fresh sieves. The hot solution is filtered and left to cool, whereupon 1-carboxyethyl 2-fluoro-4-(hexadecylamino)benzoate separates as off-white crystals.

81. Diethyl O-[2-fluoro-4-(hexadecylamino)benzoyl]tartrate

A mixture of 2-fluoro-N-trifluoroacetyl-4-(hexadecylamino)benzoyl chloride and 1.2 g. triethylamine in 100 ml. warm ether is treated with 2.5 g. diethyl tartarate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields diethyl O-[2-fluoro-4-(hexadecylamino)benzoyl]tartarate as a white, crystalline solid.

82. O-[3-Fluoro-4-(hexadecylamino)benzoyl malic acid

A warm solution of N-carbobenzyloxy-3-fluoro-4-(hexadecylamino)benzoyl chloride and 1.3 g. triethylamine in 100 ml. ether is treated with 2 g, malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% Pd(C) at 50 psi until hydrogen uptake stops. The catalyst is filtered, and the solution is evaporated. The residue is crystallized from acetic acid to yield O-[3-fluoro-4-(hexadecylamino)benzoyl]malic acid.

83. 2-(Ethoxycarbonyl)vinyl 3-fluoro-4-(hexadecylamino)benzoate

To a mixture containing 4.3 g. 1-[3-fluoro-4-(N-tert-butyloxycarbonyl-N-hexadecylamino)benzoyl]imidazole, 50 ml. 5 N sodium hydroxide is added 3 g. ethyl α-formyl acetate. The solution is vigorously stirred for 24 hours. The layers are separated, and the chloroform solution is washed once with 50 ml. 1 N sodium hydroxide. The solvent is evaporated and the residue is heated for 30 minutes at 40° C. in 50 ml. anhydrous trifluoroacetic acid. The solvent is again evaporated and the oil is crystallized from acetone to yield light yellow crystals of 2-(ethoxycarbonyl)vinyl 3-fluoro-4-(hexadecylamino)benzoate.

TABLE II

These benzoate esters are prepared from the corresponding halides, sulfonate esters, or hydroxy compounds by the methods of Examples 73–83 as shown in the table. The requisite carboxylic acids, carboxylate salts, carboxylate esters, N-protected carbonyl chlorides or N-protected carbonyl imidazoles are prepared by the methods of Examples 4–18 and 69–72.

| Example No. | Methods of Example | Compound |
| --- | --- | --- |
| 84 | 75 | Isopropyl 3-fluoro-4-(hexadecyl- |

TABLE II-continued

These benzoate esters are prepared from the corresponding halides, sulfonate esters, or hydroxy compounds by the methods of Examples 73-83 as shown in the table. The requisite carboxylic acids, carboxylate salts, carboxylate esters, N-protected carbonyl chlorides or N-protected carbonyl imidazoles are prepared by the methods of Examples 4-18 and 69-72.

| Example No. | Methods of Example | Compound |
|---|---|---|
|  |  | amino)benzoate |
| 85 | 78 | 2-Dimethylaminoethyl 2,5-difluoro-4-(undecylamino)benzoate |
| 86 | 73 | Allyl 3-chloro-4-(14-methylpentadecylamino)benzoate |
| 87 | 74 | 2,3-Epoxypropoxy 3-methoxy-4-(10-undecenylamino)benzoate |
| 88 | 73 | 4-Hydroxybutyl 2,6-difluoro-4-(4-hexadecenylamino)benzoate |
| 89 | 76 | 4-Chlorobenzyl 3-nitro-4-(4,14-pentadecadienylamino)benzoate |
| 90 | 78 | 4-(tert-Butyl)phenyl 3,5-dimethyl-4-(11-phenylundecylamino)benzoate |
| 91 | 79 | Tetrahydropyranyl 2-fluoro-4-(4-chlorobenzylamino)benzoate |
| 92 | 78 | 3-Pyridyl 3,5-dichloro-4-(1-methyl-6-heptenylamino)benzoate |
| 93 | 74 | 3-Pyridylmethyl 2-fluoro-4-(cinnamylamino)benzoate |
| 94 | 81 | 3-O-[3-fluoro-4-(11-cyclohexylundecylamino)benzoyl]glyceric acid |
| 95 | 82 | 2,6-Dichlorophenyl 3,5-difluoro-4-[6-(2-furyl)hexylamino]benzoate |
| 96 | 78 | 5-Carboxy-3-pyridyl 2-methoxy-4-(3,7,11-trimethyldodecylamino)benzoate |
| 97 | 80 | Carboxymethyl 2-fluoro-4-[2-(1-naphthyl)ethylamino]benzoate |
| 98 | 83 | 2-Carboethoxy vinyl 3-fluoro-4-(9-octadecenylamino)benzoate |
| 99 | 77 | Methyl 2,4,6-trifluoro-4-(1-methyl-6-heptenylamino)benzoate |
| 100 | 81 | 2,6-Dimethyl-3-pyridyloxy 3,6-dimethyl-4-[3-(4-benzyloxyphenyl)-propylamino]benzoate |

101. 3-Fluoro-4-(hexadecylamino)benzoylpiperidine

To a chilled solution of 35 ml. of piperidine, 2.5 ml. of triethylamine and 0.6 g. of dimethylaminopyridine in 100 ml. of diethyl ether is added (½ hour) a solution of 8.3 g. of 3-fluoro-4-hexadecylaminobenzoyl chloride hydrochloride in 50 ml. of ether. The solution is warmed to room temperature and maintained there for two hours. The solution is heated to reflux for an additional 2 hours at which time the reaction is complete. The solution is cooled, extracted twice with water and dried. The solvent is removed in vacuo and the solid is recrystallized from diethyl ether to yield 3-fluoro-4-(hexadecylamino)benzoylpiperidine.

102. Ethyl 2-fluoro-4-(hexadecylamino)hippurate

To a solution of 18.0 g. of 2-fluoro-4-(hexadecylamino)benzoic acid in a mixture of dioxane and methylenechloride is added gaseous hydrogen chloride for 10 minutes. The slurry is cooled and 18 ml. of thionyl chloride added. The slurry is brought to reflux for 2 hours and then concentrated under vacuum (thrice diluting with dioxane each time). The final amber solution is diluted with 100 ml. of dioxane and this solution added to freshly prepared ethyl glycinate in 300 ml. of methylene chloride containing 1 g. of dimethylaminopyridine and 10 ml. of triethylamide. After 16 hours at room temperature the reaction is refluxed for 2 hours, cooled and filtered. The mother liquor is extracted with water and 10% hydrochloric acid. The solution is dried and concentrated in vacuo to an amber liquid. A sample is pre-absorbed on silica and eluted with ether. Evaporation of the eluate yields a solid, which is recrystallized from acetonitrile to yield ethyl 2-fluoro-4-(hexadecylamino)hippurate as a white solid.

103. N-[2-Fluoro-4-(hexadecylamino)benzoyl]glycine

A mixture of 26.4 g. of ethyl N-[2-fluoro-4-(hexadecylamino)benzoyl]glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone to yield N-[2-fluoro-4-(hexadecylamino)benzoyl]glycine.

104. 2-Fluoro-4-(hexadecylamino)-N-phenylsulfonyl)benzamide

A solution of 31.4 g of benzenesulfonamide in 250 ml. of dry dimethylacetamide is added dropwise, with stirring and cooling, to a suspension of 5.5 g. of sodium hydride in 100 ml of dry dimethylacetamide during 30 minutes at room temperature. Stirring is continued for 30 minutes. In the meantime, a mixture of 36.2 g. of 2-fluoro-4-(hexadecylamino)benzoic acid in 100 ml of methylene chloride, 300 ml. of dimethoxyethane, and 40 ml. of thionyl chloride is refluxed for 1 hour and 15 minutes. The solution is evaporated and to the resulting oil residue is added, in one portion, the previously prepared mixture of sodium benzenesulfonamide in dimethylacetamide. The mixture is stirred for 30 minutes, without cooling, and then filtered. The filtrate is poured into 2 l. of water and 250 ml. of saturated sodium chloride solution. The product is collected by filtration and then dissolved in methylene chloride, the mixture is filtered through diatomaceous earth, and brine is added to break the emulsion. The layers are separated, the organic phase is dried and evaporated. The residue is crystallined from toluene to yield 2-fluoro-4-(hexadecylamino)-N-(phenylsulfonyl)benzamide.

105. N-[3-Fluoro-4-(hexadecylamino)benzoyl]methanesulfonamide

A solution of 25.2 g. of 3-fluoro-4-(hexadecylamino)-benzoyl chloride hydrochloride and 5.6 g. of methanesulfonamide in 250 ml. of pyridine is stirred under reflux for 2 hours and then concentrated in vacuo. The residue is partitioned between water and diethyl ether; the aqueous layer acidified with 1 N HCl, and the organic layer separated, dried (MgSO$_4$), and evaporated. Crystallization of the residual white solid from 60% aqueous acetic acid and then from methylene chloridehexane affords N-[3-fluoro-4-(hexadecylamino)benzoyl]methanesulfonamide as a white solid.

106. N-[3-Fluoro-4-(hexadecylamino)benzoyl]alanine

A solution of 4.75 g. of N-trifluoroacetyl-3-fluoro-4-(hexadecylamino)benzoyl chloride and 1.2 g. of triethylamine in 200 ml. of warm ether is treated with 1.55 g. alanine ethyl ester and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the N-[3-fluoro-4-(hexadecylamino)benzoyl]alanine as a white, crystalline solid.

107.
N-[3-fluoro-4-(hexadecylamino)benzoyl]benzamide

One gram of a 50% oil dispersion of sodium hydride is washed with petroleum ether by decantation, dried, and suspended in 5 ml. of tetrahydrofuran. To this stirred mixture is added a solution of 2.42 g. of benzamide in 5 ml. of tetrahydrofuran in one portion. An initial hydrogen evolution is observed. While stirring (30 min.), the sodium hydride gradually disappears and a white, milky, turbid mixture forms. A solution of 0.9 g. of N-trifluoroacetyl-3-fluoro-4-(hexadecylamino)-benzoyl chloride in 3 ml. of tetrahydrofuran is added dropwise during 5 minutes to the mixture. The whole milky mixture is stirred at room temperature under nitrogen for one hour. The mixture was then poured into water and extracted with ether. The ether extract is washed with water and brine and dried over sodium sulfate. Evaporation of the solvent, affords a pale yellow solid. The solid is recrystallized from ether-/acetonitrile (50/50) and then from acetonitrile to yield N-[3-fluoro-4-(hexadecylamino)benzoyl]benzamide.

108.
N-[2-Fluoro-4-(hexadecylamino)benzoyl]piperidine

To a warm solution of N-carbobenzoyloxy-[2-fluoro-4-(hexadecylamino)benzoyl chloride and 1.3 g. of triethylamine in 100 ml. ether is added 1.2 g. of piperidine. An immediate precipitate forms, the mixture is refluxed for one hour and then filtered. The solid is extracted several times with hot ether, and the ether is evaporated to yield a white solid. The solid is dissolved in tetrahydrofuran (100 ml.) and hydrogenated over 600 mg. 110% Pd-on-carbon at 50 psi. until hydrogen up-take stops. The catalyst is filtered and the filtrate evaporated. The residue is crystallized from acetic acid to yield N-[2-fluoro-4-(hexadecylamino)benzoyl]piperidine as a crystalline mass.

109.
N-(2,3-Dihydroxypropyl)-3-fluoro-4-(hexadecylamino)benzamide

To a mixture containing 4.3 g. of 1-{3-fluoro-4-[N-(tert-butyloxycarbonyl)hexadecylamino]benzoyl}-imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals of N-(2,3-dihydroxypropyl)-3-fluoro-4-(hexadecylamino)benzamide.

TABLE III

These benzamides are prepared from the corresponding amines or amine derivatives by the methods shown in the Table. The requisite carboxylate esters, N-protected carbonyl chlorides, or N-protected carbonyl imidazoles are prepared by the methods of Examples 69–72 and 102.

| Example No. | Methods of Example | Compound |
| --- | --- | --- |
| 110 | 103 | N-[2,5-Difluoro-4-(hexadecylamino)benzoyl]-2-methylanaine |
| 111 | 104 | 3-Chloro-4-(hexadecylamino)-N-(methylsulfonyl)benzamide |
| 112 | 104 | 2-Methyl-4-(hexadecylamino)-N-(p-tolylsulfonyl)benzamide |
| 113 | 102 | 3-[3-Methyl-4-(hexadecylamino)benzoyl]-4-carbethoxythiazolidine |
| 114 | 103 | 3-[3-Methyl-4-(hexadecylamino)benzoyl]-4-carboxythiazolidine |
| 115 | 106 | N-[3-Methoxy-4-(hexadecylamino)benzoyl]2-aminoethanesulfonic acid |
| 116 | 107 | 3-Methoxy-4-hexadecylamino-N-acetylbenzamide |
| 117 | 107 | 3,5-Dichloro-4-(undecylamino)-N-(p-chlorobenozyl)benzamide |
| 118 | 101 | 2-Methoxy-4-(tetradecylamino)-N-allylbenzamide |
| 119 | 101 | 3,5-Dimethyl-4-(1-methylpentadecyl-+mino)-N-propropargylbenzamide |
| 120 | 109 | 3,5-Dibromo-4-[3-(4-fluorophenyl)-propylamino]-N-(2,3-dihydroxypropyl)benzamide |
| 121 | 108 | 1-{2-Methyl-4-[(11-cyclohexylundecyl)-amino]benzoyl}piperidine |
| 122 | 109 | 2-Chloro-4-(isopropyl-1-methyl-2-heptynylamino)-N-(2,3-dihydroxypropyl)benzamide |
| 123 | 105 | 3-Fluoro-4-(13,13-dimethyltetradecyl)amino-N-(methylsulfonyl)benzamide |
| 124 | 104 | 3,5-Difluoro-4-(4,14-pentadecadienylamino)-N-phenylsulfonylbenzamide |
| 125 | 105 | 3,5-Diiodo-4-(15,15-dimethylhexadecylamino)-N-methylsulfonyl)benzamide |
| 126 | 103 | N-[3-Nitro-4-(15-methylhexadecylamino)benzoyl]glycine |
| 127 | 102 | 3-{2,3,5-Trifluoro-4-[3-(1,3-dimethylcyclohexyl)-2-propylaminobenzoyl]-4}-carboethoxythiazolidine |
| 128 | 101 | 1-[2-Methyl-4-(3,7,11,15-trimethyldecylamino)benzaoyl]piperidine |
| 129 | 107 | 3-Methoxy-4-(6-methlhexadecylamino)-N-acetylbenzamide |
| 130 | 109 | 3-Chloro-4-(3,7,11-trimethyl-2,6,10-dodecatrienylamino)-N-(3-hydroxypropyl)benzamide |
| 131 | 108 | 1-[3-Bromo-4-(1-ethltetradecylamino)benzoyl]pyrrolidine |
| 132 | 104 | 2-Acetoxy-4-(4-chlorobenzylamino)-N-(p-tolylsulfonyl)benzamide |
| 133 | 101 | 1-(2,6-Difluoro-4-benzylaminobenzoyl)piperidine |
| 134 | 106 | N-[3,5-Difluoro-4-(4-methylbenzylamino)benzoyl]-2-aminoethanesulfonic acid |
| 135 | 101 | 1-[2-Fluoro-4-(2-thienylbutylamino)benzoyl]piperidine |
| 136 | 101 | 1-[3-Fluoro-4-(p-fluorophenethylamino)benzoyl]piperidine |

137. Diethyl 2-fluoro-4-(hexadecylamino)benzoylmalonate

A solution of 26.6 g. of diethyl malonate and 10 ml. of 1,2-dimethoxyethane is added to a suspension of 4.0 g. of sodium hydride in 1,2-dimethoxyethane under argon. A solution of 17.3 g. of 2-fluoro-4-(hexadecylamino)-benzoyl chloride hydrochloride in 1,2-dimethoxyethane is then added. The reaction mixture is refluxed for 4.5 hours, cooled, poured on ice, acidified, and extracted with ether. The ether solution is washed with water and saturated sodium chloride solution, dried over anhydrous sodium sulfate and concentrated to dryness. Addition of a small amount of ethanol to the residue gives a solid which is filtered and discarded. The ethanol filtrate is concentrated and the residue is recrystallized from ether to yield diethyl 2-fluoro-4-(hexadecylamino)benzoylmalonate.

138. tert-Butyl ethyl 3-fluoro-4-(hexadecylamino)benzoylmalonate

A solution of 28.0 g. of tert-butyl ethyl malonate in 10 ml. of 1,2-dimethoxyethane is added to a suspension of 4.0 g. of sodium hydride in 1,2-dimethoxyethane under argon. A solution of 17.3 g. of 3-fluoro-4-(hexadecylamino)benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. The residue is then recrystallized from ether to yield tert-butyl ethyl 3-fluoro-4-(hexadecylamino)benzoylmalonate.

139. Ethyl 2-[2-fluoro-4-(hexadecylamino)benzoyl]acetoacetate

A solution of 21.6 g. of ethyl acetoacetate and 10 ml. of 1,2-dimethoxyethane is added to a suspension of 4.0 g. of sodium hydride in 1,2-dimethoxyethane under argon. A solution of 17.3 g. of 2-fluoro-4-(hexadecylamino)benzoyl chloride hydrochloride in 1,2-dimethoxyethane is then added. The reaction mixture is refluxed for 5 hours, cooled, poured on ice and extracted with ether. The ether solution is washed with water and saturated sodium chloride solution, dried over anhydrous sodium sulfate and concentrated to dryness. Recrystallization from ether affords ethyl 2-[2-fluoro-4-(hexadecylamino)benzoyl]-acetoacetate as a white solid.

140. Ethyl 3-fluoro-4-(hexadecylamino)benzoylmalonate

A solution of 3.0 g. of tert-butyl ethyl 3-fluoro-4-(hexadecylamino)benzoylmalonate 10 ml of trifluoroacetic acid is warmed with stirring for 3 hours. The solution is poured onto ice and neutralized with potassium hydroxide. The resulting precipitate is collected by filtration, washed with water and dried. Recrystallization from chloroform affords ethyl 3-fluoro-4-(hexadecylamino)-benzoylacetate.

141. 3-Fluoro-4-(hexadecylamino)benzoylacetic acid

Two grams of ethyl 3-fluoro-4-(hexadecylamino)benzoylacetate is added to a solution of potassium hydroxide in 50 ml. of 1:9 water-ethanol. The reaction mixture is stirred for 24 hours at room temperature. Careful neutralization with sulfuric acid gave a precipitate which is filtered, washed with water, and dried to yield 3-fluoro-4-(hexadecylamino)benzoylacetic acid.

142. 2'-Fluoro-4'-(hexadecylamino)-2-(methylsulfinyl)acetophenone

To a solution of 5.8 g. of dimethyl sulfoxide, dried over sieves, and 50 ml. of tetrahydrofuran is slowly added 28 ml. of n-butyl lithium (2.42 M in hexane). To this mixture is added 10 g. of methyl 2-fluoro-4-(hexadecylamino)benzoate in 200 ml. of tetrahydrofuran. After two hours, the reaction mixture is poured onto ice, acidified with dilute hydrochloric acid and quickly extracted with chloroform. The chloroform extract is washed with water and saturated sodium chloride solution and dried over anhydrous sodium sulfate. Concentration affords a solid which is washed with 500 ml. of hot hexane, filtered while hot and then washed with hexane. The white solid is dried in vacuo to yield 2'-fluoro-4'-(hexadecylamino)2-(methylsulfinyl)acetophenone.

143. 3'-Fluoro-4'-(hexadecylamino)-2-(phenylsulfonyl)acetophenone

A solution of 864 mg. of sodium hydride and 5.3 g. of methylphenylsulfone in 20 ml. of 1,2-dimethoxyethane is stirred at 60° C. for one hour under an atmosphere of argon. To this solution is then added a solution of 5.0 g. of methyl 3-fluoro-4-(hexadecylamino)benzoate and 50 ml. of tetrahydrofuran and the reaction mixture is stirred at 60° C. for 1.5 hours. The mixture is cooled, poured onto ice, acidified with dilute hydrochloric acid to pH 3 and then extracted with chloroform. The organic layer is separated, washed three times with water and saturated sodium chloride solution, dried over anhydrous sodium sulfate and then concentrated to dryness. The crude solid is chromatographed on silica gel, eluting with methylene chloride to yield 3'-fluoro-4'-(hexadecylamino)-2-(phenylsulfonyl)acetophenone.

144. 3'-Fluoro-4'-(hexadecylamino)-2-(phenylsulfinyl)acetophenone

To a solution of 6.2 g. of methylphenylsulfoxide, dried over sieves, and 50 ml. of tetrahydrofuran is slowly added 28 ml. of n-butyl lithium (2.42 M in hexane). To this mixture is added 10 g. of methyl 3-fluoro-4-(hexadecylamino)benzoate in 200 ml. of tetrahydrofuran. After two hours, the reaction mixture is poured into ice, acidified with diluted hydrochloric acid and quickly extracted with chloroform. The chloroform layer is washed with water and saturated sodium chloride solution and dried over anhydrous sodium sulfate. Concentration affords a solid which is washed with 500 ml. of hot hexane, filtered while hot, and then washed with 50 ml. of hexane. The white solid is dried in vacuo yielding 3'-fluoro-4'-(hexadecylamino)-2-(phenylsulfinyl)acetophenone.

145. 3-[2-Fluoro-4-(hexadecylamino)benzoyl]-2,4-pentadedione

A solution of 28.4 g. of 2-4-pentanedione and 20 ml. of 1,2-dimethoxyethane is added to a suspension of 13.6 g. of sodium hydride in 220 ml. of 1,2-dimethoxyethane under argon. A solution of 28.7 g. of 3-fluoro-4-(hexadecylamino)benzoyl chloride hydrochloride in 1,2-dimethoxyethane is added. The reaction mixture is stirred at room temperature for 12 hours, cooled, poured on ice and extracted with ether. The ether solution is washed with water and saturated sodium chloride solution, dried over anhydrous sodium sulfate and concentrated. The residue is then chromatographed over silica gel to yield 3-[2-fluoro-4-(hexadecylamino)-benzoyl]2,4-pentanedione.

146. Methyl 3-[2-fluoro-4-(hexadecylamino)benzoyl]propionate

A mixture of 35 g. of 3-(2-fluoro-4-acetamidobenzoyl)propionic acid, 700 ml. of methanol and 1.4 ml. of concentrated sulfuric acid is refluxed for 76 hours. The solution is cooled to 35° C. and poured onto 7 g. of anhydrous sodium acetate while stirring. The reaction mixture is stirred in an ice-bath. The solid is collected and washed with cold methanol to yield methyl 3-(2-fluoro-4-aminobenzoyl)propionate as a white solid. A mixture of this solid, 9.2 g. of hexadecyl bromide and 4.2 g. of potassium carbonate is stirred for 20 hours at 125° C. under nitrogen. The mixture is then cooled to 25° C. and 30 ml. of water is added. After stirring, the product is filtered and washed with water. Recrystallization from methanol affords methyl 3-[2-fluoro-4-(hexadecylamino)benzoyl]propionate as a white solid.

147. 3-[2-Fluoro-4-(hexadecylamino)benzoyl]propionic acid

A solution of 5.4 g. of methyl 3-[2-fluoro-4-(hexadecylamino)benzoyl]propionate is stirred with 5.4 g. of potassium hydroxide in 100 ml. of 95% ethanol for 3 hours at reflux. The reaction mixture is cooled, diluted with 50 ml. of ethanol and 100 ml. of water, and neutralized with hydrochloric acid. The solution is cooled to room temperature and filtered. The white solid is washed with 50% aqueous ethanol and dried. The product is recrystallized from ethanol to yield 3-[2-fluoro-4-(hexadecylamino)benzoyl]propionic acid as a white crystalline solid.

TABLE IV

Some of these acetophenone derivatives are prepared by reactions of either acid chloride hydrochlorides obtained in the manner of Example 69, or methyl esters, obtained in the manner of Example 5, with appropriate anionic acylatable substrates. Others are obtained by alkylations of preformed acetophenones, in the manner of Example 146, or by chemical transformations of various acetophenones, in the manner of Examples 140, 141 or 147.

| Example No. | Method of Example | Compound |
|---|---|---|
| 148 | 137 | Diethyl 2,6-difluoro-4-(undecylamino)benzoylmalonate |
| 149 | 139 | Ethyl 2,3,5-trifluoro-4-(tetradecylamino)benzoylacetoacetate |
| 150 | 140 | Ethyl 2-chloro-4-(1-methylpentadecylamino)benzoylacetate |
| 151 | 141 | 2-Chloro-4-(1-methylpentadecylamino)benzoylacetic acid |
| 152 | 138 | tert-Butyl ethyl 3-chloro-4-(3,7,11-trimethyldodecylamino)benzoylmalonate |
| 153 | 143 | 3′,5′-Dimethyl-4′-(15,15-dimethylhexadecylamino)-2-(p-tolylsulfonyl)-acetophenone |
| 154 | 142 | 3′,5′-Dichloro-4′-(1-methyl-6-heptenylamine)-2-(methylsulfinyl)acetophenone |
| 155 | 146 | Methyl 3-[3-methyl-4-(4-hexadecenylamino)benzoyl]propionate |
| 156 | 147 | 3-[3-Methyl-4-(4-hexadecenylamino)benzoyl]propionic acid |
| 157 | 145 | 3-[3-Nitro-4-(9-octadecenylamino)benzoyl]-2,4-pentanedione |
| 158 | 142 | 3′-Fluoro-4′-(4-chlorobenzylamino)-2-(methylsulfinyl)acetophenone |
| 159 | 140 | Ethyl 2-chloro-4-(11-cyclohexylundecylamino)benzoyl acetate |
| 160 | 145 | 3-[2,6-Difluoro-4-(4-decyloxybenzylamino)benzoyl]-2,4-pentanedione |
| 161 | 146 | Methyl 3-[2-methoxy-4-(4-methylbenzylamino)benzoyl]propionate |
| 162 | 147 | 3-[3,5-Dichloro-4-(cinnamylamino)-benzoyl]propionic acid |
| 163 | 143 | 3′-Fluoro-4′-[4-(2-thienyl)butylamino]2-(phenylsulfonyl)acetophenone |
| 164 | 137 | Diethyl 3-bromo-4-[(4-cyclohexyl-2-butenyl)amino]benzoylmalonate |
| 165 | 139 | Ethyl 2,3,5,6-tetrafluoro-4-[3-(3-trifluoromethylphenyl)propylamino]-benzoylmalonate |
| 166 | 138 | tert-Butyl ethyl 2-methoxy-4-(4-fluorobenzylamino)benzoylmalonate |
| 167 | 138 | tert-Butyl ethyl 3,5-dimethyl-4-[6-(2-furyl)hexylamino]benzoylmalonate |
| 168 | 140 | Ethyl 2,5-difluoro-4-[2-(1-naphthyl)ethylamino]benzoylacetate |
| 169 | 144 | 3′,5′-Diiodo-4′-(cyclotetradecylamino)-2-(p-tolylsulfinyl)acetophenone |
| 170 | 147 | 4-[2-Fluoro-4-(tetradecylamino)-benzoyl]butyric acid |
| 171 | 142 | 2′,3′,6′-Trifluoro-4′-(3,7,11-trimethyldodecylamino)-2-(methylsulfinyl)acetophenone |
| 172 | 141 | 3-[4-(tert-butylbenzylamino)-2-fluorobenzoylacetic acid |

173. Ethyl 2-fluoro-4-(hexadecylamino)phenylacetate

A solution of 8.2 g. of 2-fluoro-4-aminophenylacetic acid, 150 ml. of absolute ethanol, and 3 ml. of boron trifluoride etherate is heated to reflux for 15 hours. The solution is concentrated by distillation and then evaporated to dryness in vacuo. The residue is dissolved in ethyl ether, washed with aqueous sodium bicarbonate dried and evaporated to yield ethyl 2-fluoro-4-aminophenylacetate. A mixture of 5.0 g. of this amine, 9.4 g. of 1-bromohexadecane, 4.2 g. of anhydrous potassium carbonate and 40 ml. of hexamethylphosphoramide is heated at 80° C. for 7 hours. The mixture is then cooled, diluted with water, and extracted with ethyl ether. The ether extracts are washed with water, dried and evaporated. The residue is recrystallized from a mixture of chloroform and hexane, yielding ethyl 2-fluoro-4-(hexadecylamino)phenylacetate.

174. 2-Fluoro-4-(hexadecylamino)phenylacetic acid

A mixture of 6.0 g. of ethyl 2-fluoro-4-(hexadecylamino)phenylacetate, 7.0 g. of potassium hydroxide and 100 ml. of ethanol-water is heated to reflux for 4 hours. While hot, the mixture is adjusted to pH 7 with conc. hydrochloric acid. The mixture is diluted with water, cooled and filtered. Recrystallization of the precipitate yields 2-fluoro-4-(hexadecylamino)phenylacetic acid.

175. Ethyl 3-fluoro-4-aminohydrocinnamate

A mixture of 5.0 g. of 3-fluoro-4-nitrocinnamic acid and 100 mg. of 10% palladium-on-carbon in 200 ml. of ethanol containing 5 drops of 5.5 N ethanolic hydrogen chloride is treated with hydrogen in a Parr apparatus at room temperature for 3 hours. The mixture is then filtered through Celite and the filtrate is concentrated, affording 3-fluoro-4-aminohydrocinnamic acid.

A solution of 3-fluoro-4-aminohydrocinnamic acid in 100 ml. of absolute ethanol containing 16 ml. of boron trifluoride etherate is heated to reflux for 48 hours. The solution is then cooled, poured into 5% aqueous sodium carbonate and extracted with methylene chloride. Evaporation of the organic extracts yields ethyl 3-fluoro-4-aminohydrocinnamate. CL 176. 3-Fluoro-4-(hexadecylamino)hydrocinnamic acid In a manner directly analogous to that described in Example 9, ethyl 3-fluoro-4-aminohydrocinnamate is alkylated with hexadecyl bromide to form ethyl 3-fluoro-4-(hexadecylamino)hydrocinnamate. Subsequently, in a manner directly analogous to that described in Example 10, ethyl 3-fluoro-4-(hexadecylamino)hydrocinnamate is hydrolyzed to 3-fluoro-4-(hexadecylamino)hydrocinnamic acid.

177. 2-Fluoro-4-(hexadecylamino)cinnamic acid

A mixture of ethyl 2-fluoro-4-aminocinnamate, one equivalent of 1-bromohexadecane and one equivalent of anhydrous potassium carbonate in hexamethylphosphoramide is heated for 20 hours at 60° C. The mixture is then cooled, diluted with water and extracted with ether. The combined ether extracts are dried, filtered and evaporated to provide ethyl 4-hexadecylaminocinnamate. The ester is hydrolyzed with sodium hydroxide in a 1:9 water:ethanol solution at steam bath temperatures for 10 hours. The hot solution is then acidified with acetic acid, cooled and filtered and the solid is washed with water. Recrystallization from chloroform yields 2-fluoro-4-(hexadecylamino)cinnamic acid.

178. 2-Fluoro-4-(hexadecylamino)phenylpropiolic acid

A sample of 50 g. of ethyl 2-fluoro-4-aminocinnamate is dissolved in 500 ml. of ethyl ether and a solution of 28 g. of trifluoroacetic anhydride in 30 ml. of ether is added dropwise. When the addition is complete, the reaction is allowed to stir for another hour. The mixture is then diluted with hexane and filtered, providing ethyl 2-fluoro-4-trifluoroacetamidocinnamate.

A solution of 40 g. of ethyl 2-fluoro-4-trifluoroacetamido cinnamate in 200 ml. of carbon tetrachloride is cooled in ice. Bromine (28 g.) is added dropwise, the reaction is allowed to stir for one additional hour and then the solvent is evaporated. The crystalline residue is the dibromo ester.

A solution of 11.4 g. of potassium hydroxide in 300 ml. of 95% ethanol is cooled to 40° C. and 20 g. of the crude dibromo ester above is added. After 30 minutes, the reaction is heated to reflux for five hours. The solution is then cooled and filtered. The filtrate is treated with acetic acid until the solution is neutral to litmus, then concentrated, chilled and filtered, to yield 2-fluoro-4-aminophenylpropiolic acid.

Alternatively, the 2-fluoro-4-aminophenylpropiolic acid is prepared from 2-fluoro-4-nitrocinnamic acid by successive treatment with bromine in acetic acid, aqueous sodium hydroxide, ferric sulfate and ammonium hydroxide, and ethanolic hydrogen chloride. The propiolic acid is then converted to the corresponding ethyl ester and alkylated with 1-bromohexadecane in the manner of Example 9. The resulting ethyl 2-fluoro-4-(hexadecylamino)phenylpropiolate is hydrolyzed in the manner of Example 10 to yield 2-fluoro-4-(hexadecylamino)phenylpropiolic acid.

I claim:

1. The method of inhibiting atherosclerotic lesion development in a mammal comprising the administration of an effective lesion-development inhibiting amount of a compound of the formula:

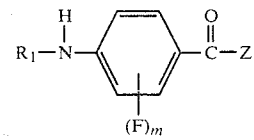

wherein $R_1$ is an unbranched or branched alkyl group, optionally mono- or polyunsaturated and optionally containing saturated or unsaturated cycloalkyl and/or substituted or unsubstituted aryl or heteroaryl groups, of the formula $C_nH_{2n-(2p-1)}$, n is an integer from 7 to 19, inclusive, and p is an integer up to 6; m is an integer from 1 to 4, inclusive; Z is selected from the group consisting of hydrogen, loweralkyl, hydroxy, loweralkoxy, loweralkoxyalkoxy, diloweralkylaminoalkoxy, (mono- or polyhydroxy)loweralkoxy, allyloxy, 2,3-epoxypropoxy, substituted or unsubstituted benzyloxy, substituted or unsubstituted phenoxy and 3-pyridyloxy, pyridylmethoxy, (mono- or polycarboxy)loweralkoxy, (mono- or polycarboxy)hydroxyloweralkoxy, tetrahydropyranyloxy, (mono- or polyhydroxy)alkylamino, allylamino, propargylamino, 2-sulfoethylamino, (mono- or polycarboxy)loweralkylamino, (mono- or polycarboalkoxy)loweralkylamino, loweralkanoylamino, (substituted or unsubstituted aroyl)amino, loweralkanesulfonylamino, (substituted or unsubstituted arene)-sulfonylamino, loweralkanoylhydrazino, hydroxylamino, polymethyleneimino, 4-carboethoxy or 4-carboxythiazolidino, loweralkyl bearing one or more carboxy, carboalkoxy, carbamoyl, acyl, sulfinyl, or sulfonyl groups; and wherein

may be replaced by carboxyloweralkyl, carboxyloweralkenyl, carboxyloweralkynyl, carboalkoxyloweralkyl, carboalkoxyloweralkenyl, carboalkoxyloweralkynyl, and the pharmacologically acceptable acid addition and cationic salts thereof to said mammal.

2. The method of inhibiting atherosclerotic lesion development in a mammal comprising the administration of an effective lesion-development inhibiting amount of a compound of the formula:

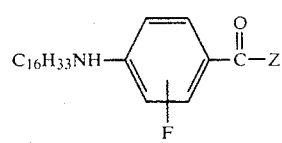

wherein $C_{16}H_{33}$ represents an unbranched or branched hexadecyl group and Z is selected from the group consisting of hydroxy, hydrogen, 2,3-dihydroxypropyloxy, carboxymethoxy, loweralkanesulfonylamino, substituted or unsubstituted arenesulfonylamino, loweralkanoylamino, (substituted or unsubstituted aroyl)amino, carboxyalkylamino, or 1-sulfoethylamino, and the pharmacologically acceptable acid-addition and cationic salts thereof to said mammal.

3. The method of claim 1, wherein said compound is administered to provide a daily dosage of from about one mg. to about 250 mg. per kilogram of body weight of said mammal.

4. The method of claim 2, wherein said compound is administered to provide a daily dosage of from about one mg. to about 250 mg. per kilogram of body weight of said mammal.

5. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 1.

6. An antiatherosclerotic composition in dosage-unit form useful for preventing or diminishing atherosclerotic lesion formation in mammals comprising from about one mg. to about 250 mg. per kilogram of body weight per daily dosage unit of a compound of claim 2.

7. The method of inducing regression of atherosclerotic lesion development in a mammal comprising administering to said mammal an effective lesion-regressive amount of a compound of claim 1.

8. The method of inducing regression of atherosclerotic lesion development in a mammal comprising administering to said mammal an effective lesion-regressive amount of a compound of claim 2.

9. The method of claim 7, wherein said compound is administered to provide a daily dosage of from about one mg. to about 250 mg. per kilogram of body weight of said mammal.

10. The method of claim 8, wherein said compound is administered to provide a daily dosage of from about one mg. to about 250 mg. per kilogram of body weight of said mammal.

11. The method of treating hyperlipidemia and hyperlipoproteinemia and/or altering the lipoprotein pattern in a mammal comprising administration to said mammal an effective lipid-altering amount of a compound of claim 1.

12. The method of treating hyperlipidemia and hyperlipoproteinemia and/or altering the lipoprotein pattern in a mammal comprising administration to said mammal an effective lipid-altering amount of a compound of claim 2.

* * * * *